(12) United States Patent
Taylor et al.

(10) Patent No.: US 6,315,715 B1
(45) Date of Patent: Nov. 13, 2001

(54) FLEXIBLE INNER LINER FOR THE WORKING CHANNEL OF AN ENDOSCOPE

(75) Inventors: James M. Taylor, Mountain View; Phil Pesta, San Jose, both of CA (US)

(73) Assignee: Modified Polymer Components, Inc., Sunnyvale, CA (US)

( * ) Notice: Subject to any disclaimer, the term of this patent is extended or adjusted under 35 U.S.C. 154(b) by 0 days.

(21) Appl. No.: 09/377,338

(22) Filed: Aug. 17, 1999

Related U.S. Application Data

(63) Continuation of application No. 08/746,249, filed on Nov. 7, 1996, now Pat. No. 5,938,587.
(60) Provisional application No. 60/016,216, filed on Apr. 25, 1996.

(51) Int. Cl.[7] ........................................ A61B 1/00
(52) U.S. Cl. ..................... 600/140; 600/123; 138/122; 138/173
(58) Field of Search ..................... 600/139, 140, 600/123, 153, 155; 138/121, 122, 173

(56) References Cited

U.S. PATENT DOCUMENTS

| | | | |
|---|---|---|---|
| 2,897,840 | * | 8/1959 | Roberts et al. ........................ 138/56 |
| 3,580,289 | * | 5/1971 | James, Jr. ............................. 138/125 |
| 3,891,007 | * | 6/1975 | Kleykamp ............................. 138/121 |
| 4,742,817 | * | 5/1988 | Kawashima et al. .................... 128/4 |
| 4,807,598 | * | 2/1989 | Hasegawa ................................ 128/6 |
| 5,125,395 | * | 6/1992 | Adair ...................................... 128/4 |
| 5,520,222 | * | 5/1996 | Chikama .............................. 138/118 |
| 5,915,736 | * | 6/1999 | Marik et al. ........................ 285/21.3 |
| 5,938,587 | * | 8/1999 | Taylor et al. ......................... 600/139 |

* cited by examiner

*Primary Examiner*—Linda C. M. Dvorak
*Assistant Examiner*—Jocelyn D Ram
(74) *Attorney, Agent, or Firm*—James J. Leary; Carol D. Titus

(57) ABSTRACT

A tubular member useful as an inner liner for the working channel of a flexible endoscope has a distal portion which is specially treated to make it highly flexible and resistant to kinking or collapsing when it bends with the flexible section of the endoscope. The tubular member is also useful as a catheter device or as a component of a catheter device or catheter system. A multiplicity of external ridges on the distal portion of the tubular member reinforce the tubing wall and prevent kinking or buckling of the wall or collapsing of the inner lumen. The external ridges may be formed by convolutions of the tubing wall or by external threads which are formed on the exterior of the tubing wall within the flexible distal portion. An outer helical reinforcing coil may be added between the external ridges to further reinforce the flexible distal portion of the tubular member from kinking or collapsing. The flexible distal portion of the tubular member may be coated with a layer of a flexible polymer to fill in the spaces between the external ridges and to cover the helical reinforcing coil. Manufacturing methods for the tubular member are also disclosed.

22 Claims, 14 Drawing Sheets

FLEXIBLE INNER LINER FOR THE WORKING CHANNEL OF AN ENDOSCOPE

RELATIONSHIP TO OTHER APPLICATIONS

This application is a continuation of U.S. Pat. No. 08/746,249, filed Nov. 7, 1996, now U.S. Pat. No. 5,938,587, which claims the benefit of U.S. Provisional Patent Application No. 60/016,216, filed Apr. 25, 1996.

FIELD OF THE INVENTION

The present invention relates generally to endoscopes for diagnostic and therapeutic medical applications, as well as borescopes for industrial applications. More particularly, it relates to a disposable flexible inner liner for the working channel of a flexible endoscope or borescope. The present invention also relates to catheters for insertion into a body lumen or cavity with or without the guidance of an endoscope.

BACKGROUND OF THE INVENTION

Endoscopes are frequently used in a medical setting for diagnostic and therapeutic procedures. Borescopes, their industrial counterpart, are frequently used in industrial settings for internal inspection of machines and manufactured parts. Endoscopes and borescopes are sometimes manufactured with one or more working channels through the scope for passing instrumentation through for performing diagnostic or therapeutic procedures within the field of view of the scope. The working channel in an endoscope is also sometimes referred to as the biopsy channel of the scope. It is common to use an inner liner within the working channel of endoscopes and borescopes. Sometimes, the inner liner is a single-use, disposable item. The inner liner provides a low friction surface to facilitate passage of instruments and helps to avoid damage to the interior of the scope by the instruments as they pass through the working channel. The inner liner also helps to avoid contamination of the interior of the scope by the instruments as they pass through the working channel. This is especially important in medical applications where the small diameter working channels may be difficult to clean and sterilize between uses. A sterile, disposable inner liner can be used to keep the working channel of the endoscope clean. For rigid endoscopes and borescopes, which typically use rod optics for image transfer through the scope, the working channel can be lined with a simple thin-walled tube without concern for the flexibility of the liner. However, for flexible endoscopes and borescopes, which use flexible fiberoptics for image transfer through the scope, the inner liner for the working channel must be sufficiently flexible to bend with the scope without kinking or collapsing, which would compromise the inner lumen of the working channel. Flexible endoscopes and borescopes may be made flexible along their entire length or they may be made with a flexible distal section and a relatively rigid proximal section. It is important that the flexible portion of the working channel liner be at least as long as the flexible section of the scope for which it is intended. The present invention provides an improved flexible inner liner for the working channel of flexible endoscopes and borescopes. For the sake of brevity, endoscopes and borescopes will both be referred to as endoscopes in the following detailed description of the invention. However, it should be kept in mind that, except where specifically stated to the contrary, the description and the accompanying comments apply equally well to medical endoscopes and to industrial borescopes.

Another technical area relevant to the present invention involves catheters. The term "catheter" embraces a wide variety of elongated, generally tubular, devices for insertion into a body lumen or cavity for diagnostic or therapeutic purposes. These include inter alia cardiovascular catheters, urology catheters, visceral catheters and catheter introducers. Catheters can be introduced into the body through the working channel of an endoscope or they can be introduced independently under endoscopic, fluoroscopic or ultrasonic guidance. The construction of the disposable flexible inner liner of the present invention will also be beneficial for the construction of many varieties of catheters.

SUMMARY OF THE INVENTION

In accordance with the foregoing discussion, the present invention takes the form of an elongated tubular inner liner for the working channel of a flexible endoscope. At least a portion of the length of the elongated tubular inner liner is highly flexible so that it will freely bend with the flexible section of the endoscope. The flexible portion of the inner liner is specially treated to make it resistant to kinking or collapse when it bends with the flexible section of the endoscope. Various means are disclosed for treating the flexible portion to make it flexible and kink resistant. A first embodiment of the flexible endoscope liner has a convoluted flexible distal portion. In a second embodiment, the convoluted flexible distal portion has an additional outer layer of a flexible polymer. A third embodiment of the flexible endoscope liner has a helically convoluted flexible distal portion with an outer helical reinforcing coil. In a fourth embodiment, the helically convoluted flexible distal portion has a helical reinforcing coil and an outer layer of a flexible polymer. A fifth embodiment of the flexible endoscope liner has a helically threaded flexible distal portion. In a sixth embodiment, the helically threaded flexible distal portion has an outer layer of a flexible polymer. In a seventh embodiment, the helically threaded flexible distal portion has an outer helical reinforcing coil. In an eighth embodiment, the helically threaded flexible distal portion has a helical reinforcing coil and an outer layer of a flexible polymer. Manufacturing methods for each of the embodiments are also disclosed.

The various constructions and manufacturing methods described for the disposable flexible inner liner of the present invention will also be advantageous for constructing a flexible tubular member for use in a variety of catheters. The flexible tubular member may be used alone, without significant modification, as a diagnostic or therapeutic catheter, a guiding catheter or a catheter introducer. Alternatively, the flexible tubular member may also be used as one component of a more complex catheter device or a catheter system. A flexible tubular member built according to the disposable flexible inner liner construction will be especially useful as a catheter component where the advantages of flexibility, kink resistance and an uncompromised inner lumen are important to the catheter performance.

DETAILED DESCRIPTION OF THE INVENTION

Figure 1A:
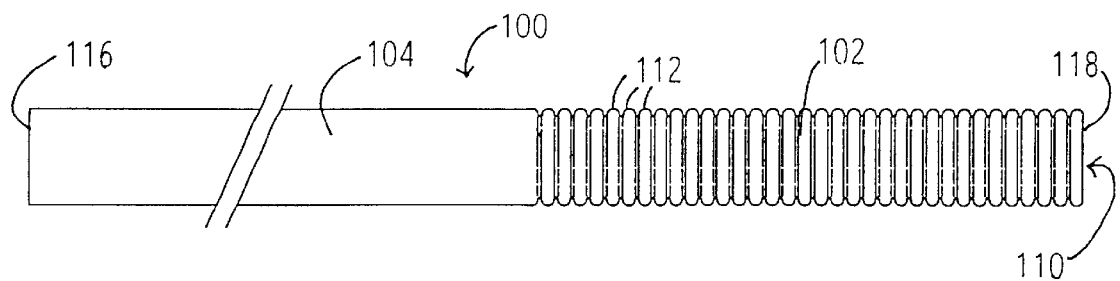
FIG. 1A shows a first embodiment of the flexible endoscope liner having a convoluted flexible distal portion.

FIG. 1A shows a first embodiment of the flexible endoscope liner 100 of the present invention. In this exemplary embodiment, the flexible endoscope liner 100 is an elongated tubular member which includes a convoluted flexible distal portion 102 and a relatively inflexible proximal portion 104. The flexible endoscope liner 100 has a tubular construction with an inner lumen 110 which extends from the proximal end 116 to the distal end 118 of the flexible endoscope liner 100 through the relatively inflexible proximal portion 104 and the convoluted flexible distal portion 102. The convoluted flexible distal portion 102 of the flexible endoscope liner 100 is specially treated to increase its flexibility and to make it resistant to kinking or collapse when it bends with the flexible section of the endoscope. The overall length of the flexible endoscope liner 100 is made to match the length of the working channel of the endoscope for which it is intended. The convoluted flexible distal portion 102 should be at least as long as the flexible section of the endoscope, with the relatively inflexible proximal portion 104 making up the remainder of the length. Typically, the overall length of the flexible endoscope liner 100 is between 30 and 250 cm, and the length of the convoluted flexible distal portion 102 is typically between 4 and 25 cm, but can extend the full length of the device. It should be noted that these length dimensions are highly variable, depending on the actual design of the endoscope. For use with flexible endoscopes which are flexible along their entire length, the convoluted flexible distal portion 102 may extend the full length of the flexible endoscope liner 100 and the relatively inflexible proximal portion 104 may be totally absent.

Figure 1B:
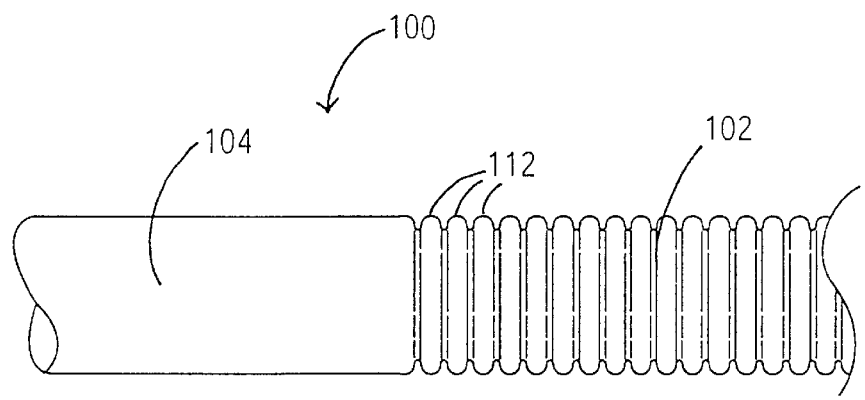
FIG. 1B is an enlarged detail view of the convoluted flexible distal portion of the flexible endoscope liner of FIG. 1A.
Figure 1C:
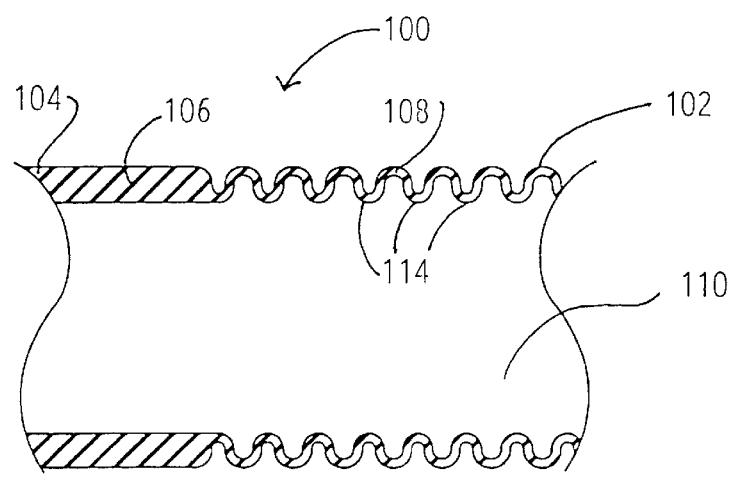
FIG. 1C is a cross section of the convoluted flexible distal portion of the flexible endoscope liner of FIG. 1A.

FIG. 1B is an enlarged detail view of the flexible endoscope liner 100 of FIG. 1A showing the transition between the relatively inflexible proximal portion 104 and the convoluted flexible distal portion 102. FIG. 1C shows a longitudinal cross section of the transition between the relatively inflexible proximal portion 104 and the convoluted flexible distal portion 102 of the flexible endoscope liner 100. The inner lumen 110 is continuous through the relatively inflexible proximal portion 104 and the convoluted flexible distal portion 102 of the flexible endoscope liner 100. In the relatively inflexible proximal portion 104 of the flexible endoscope liner 100, the inner lumen 110 is surrounded by a tubular proximal wall 106. In the convoluted flexible distal portion 102 of the flexible endoscope liner 100, the inner lumen 110 is surrounded by a tubular distal wall 108 which is folded into a convoluted configuration to increase its flexibility and to make it resistant to kinking or collapse so that the internal diameter of the inner lumen 110 is not compromised when it bends with the flexible section of the endoscope.

In one preferred embodiment of the invention, the internal diameter of the inner lumen 110 and the external diameter of the flexible endoscope liner 100 remain relatively constant throughout the length of the relatively inflexible proximal portion 104 and the convoluted flexible distal portion 102 of the flexible endoscope liner 100. To accomplish this, the relatively inflexible proximal portion 104 is made with a relatively thick proximal wall 106 and a relatively thinner distal wall 108 so that the distal wall 108 can follow the convolutions and maintain the same external diameter at the peaks of the convolutions 112 and the same internal diameter at the troughs of the convolutions 114 as the thicker proximal wall 106. Typically, the relatively thinner distal wall 108 will have approximately 30–70 percent of the wall thickness of the thicker proximal wall 106. Typical embodiments of the flexible endoscope liner 100 will have a proximal portion 104 and a flexible distal portion 102 with an internal diameter of approximately 1.8–4.0 mm and an external diameter of approximately 2.0–4.5 mm. However, the internal diameter and external diameter can vary widely depending on the actual design of the endoscope for which the flexible endoscope liner 100 is intended. In this illustrative embodiment, the proximal wall 106 and the distal wall 108 are made from a continuous polymeric material. In other possible embodiments, the proximal wall 106 and the distal wall 108 may be made from dissimilar materials. Many different polymeric materials are suitable for construction of the proximal wall 106 and the distal wall 108 of the flexible endoscope liner 100, including highly lubricious polymers, such as fluoropolymers (e.g. PTFE, EPTFE, PFA) and polyolefins, like polyethylene (e.g. LDPE, HDPE), polypropylene and polyolefin copolymers; high strength polymers, such as polyamides (e.g. nylon 11, nylon 12, polyamide copolymers); thermoplastic elastomers (e.g. polyurethane); and thermoset polymers. Alternatively, the proximal wall 106 and/or the distal wall 108 of the flexible endoscope liner 100 may be made from a composite material, for example a thermoplastic or thermoset polymer matrix with wire or fiber reinforcement which may be braided, spiral wound, counterwound or randomly oriented within the matrix material. Additionally, the proximal wall 106 and/or the distal wall 108 may be made from multiple layers of tubing. For example, the flexible endoscope liner 100 may be made with an inner tubular layer of a highly lubricious polymer and an outer tubular layer of a polymer chosen for another desirable property, such as high strength or flexibility. Advantageously, lubricious coatings may also be added to the interior and/or exterior surfaces of the flexible endoscope liner 100.

Figure 2A:
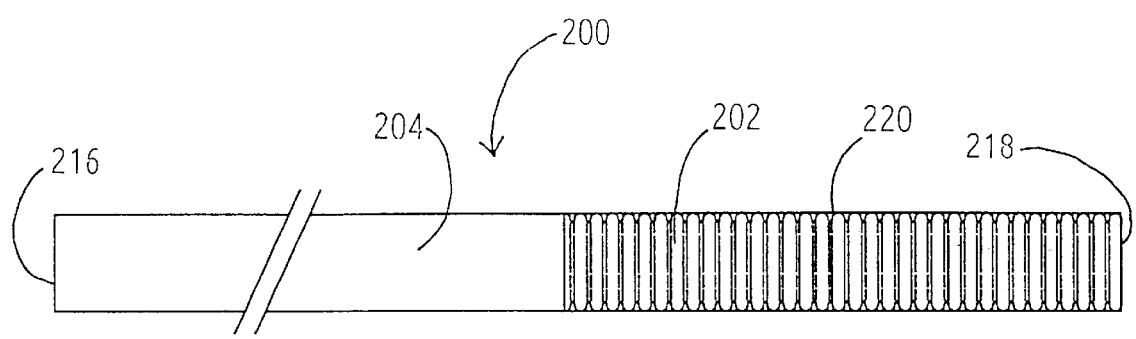
FIG. 2A shows a second embodiment of the flexible endoscope liner with a convoluted flexible distal portion having an outer layer of a flexible polymer.
Figure 2B:
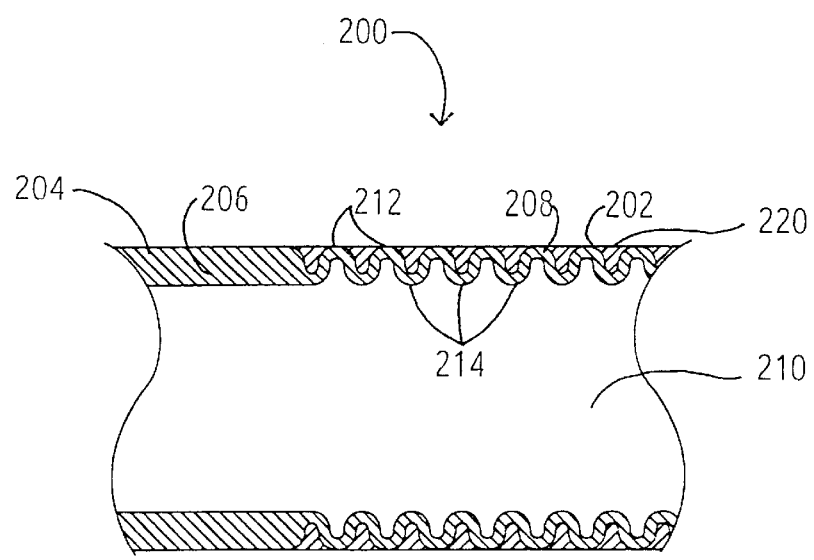
FIG. 2B is a cross section of the flexible distal portion of the flexible endoscope liner of FIG. 2A.

FIG. 2A shows a second embodiment of the flexible endoscope liner 200 which is a modification of the flexible endoscope liner 100 shown in FIG. 1A. Similar to the previously described embodiment, the flexible endoscope liner 200 is an elongated tubular member with an inner lumen 210 which extends from the proximal end 216 to the distal end 218. The flexible endoscope liner 200 includes a relatively inflexible proximal portion 104 having a relatively thick proximal wall 206 and a convoluted flexible distal portion 202 having a thinner distal wall 208 which is folded into a convoluted configuration. FIG. 2B shows a longitudinal cross section of the transition between the relatively inflexible proximal portion 204 and the convoluted flexible distal portion 202 of the flexible endoscope liner 200. The convoluted flexible distal portion 202 of the flexible endoscope liner 200 has an additional outer layer 220 of a flexible polymer. The flexible outer layer 220 fills in between the peaks of the convolutions 212 on the convoluted flexible distal portion 202 to create a smooth exterior surface. Preferred materials for the flexible outer layer 220 include flexible thermoplastic elastomers, such as ethylene vinyl acetate (EVA) or polyamide copolymers (e.g. PEBAX from ELF ATOCHEM) and thermoplastic polyurethanes and flexible thermoset polymers, such as silicone, latex or thermoset polyurethanes. The hardness of the flexible outer layer 220 material can vary from approximately 50 Shore A durometer to approximately 35 Shore D durometer.

Figure 3A:
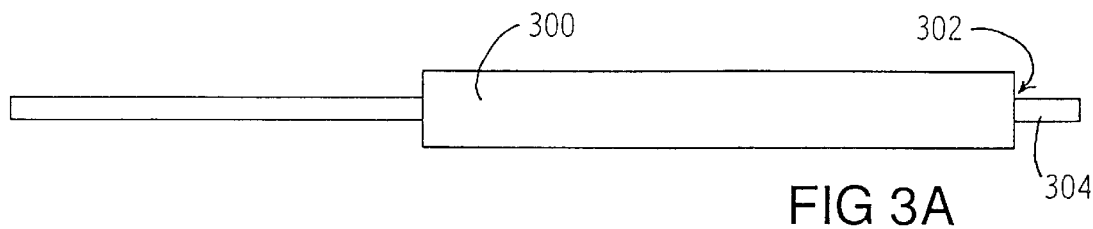
FIGS. 3A, 3B, 3C and 3D are a series of drawings showing the fabrication steps for the flexible endoscope liners of FIGS. 1A and 2A.
Figure 3B:
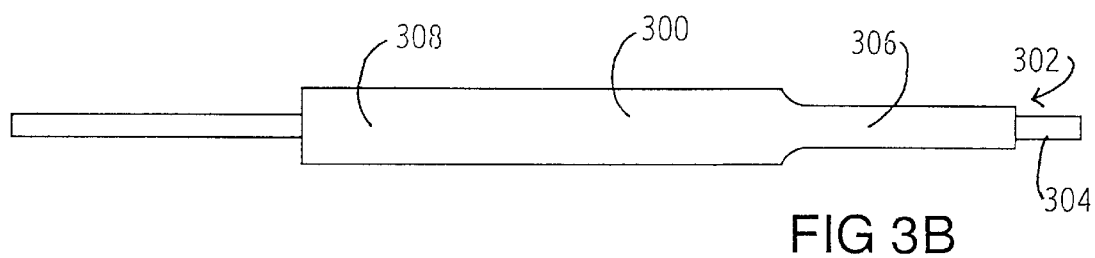
Figure 3C:
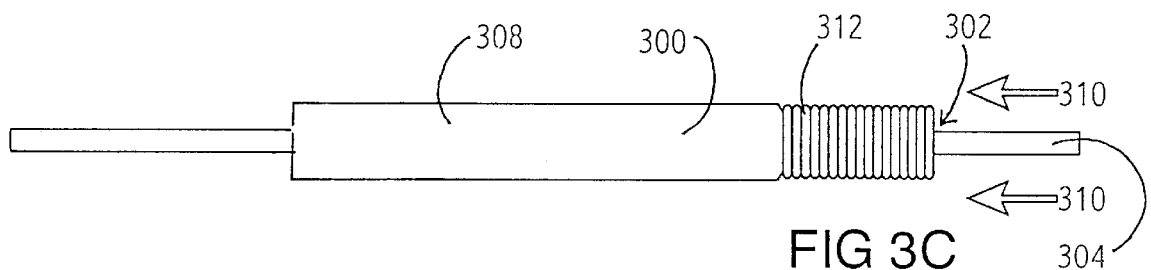
Figure 3D:
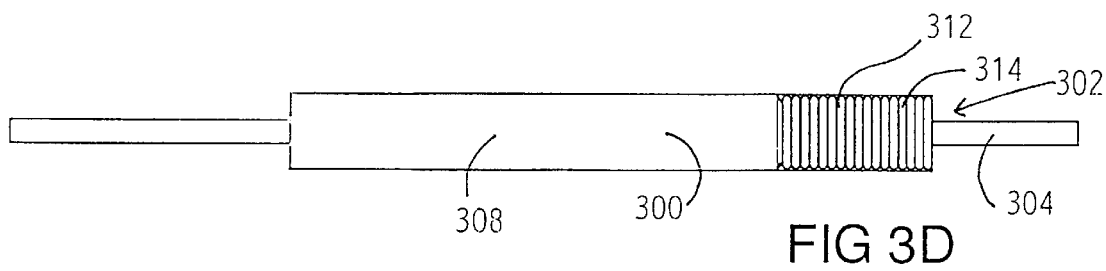

FIGS. 3A, 3B, 3C and 3D are a series of drawings illustrating one preferred method for fabricating the flexible endoscope liners of FIGS. 1A and 2A. In the first step of the fabrication method shown in FIG. 3A, an extruded polymer tube 300 is cut to an appropriate length and a straightened wire mandrel 304 is inserted into the inner lumen 302 of the tube 300. The wire mandrel 304 is preferably made of stainless steel or another nontoxic, high strength material. The external diameter of the wire mandrel 304 should closely match the internal diameter of the inner lumen 302 with only about 1–3 thousandths of an inch clearance. A nontoxic lubricant or a lubricious coating, such as PTFE, may be used on the wire mandrel 304 to allow easy insertion and removal. In the second step, shown in FIG. 3B, one end of the tube 300 is drawn to reduce its external diameter, thereby creating a drawn distal portion 306 and an undrawn proximal portion 308. The drawing step may be performed by various means appropriate for the material chosen for the extruded polymer tube 300. The drawn distal portion 306 may be created by stretching one end of the extruded polymer tube 300 by hand or by machine, either at room temperature or at an elevated temperature. Alternatively, the drawn distal portion 306 may be created by pulling one end of the extruded polymer tube 300 through a tapered die by hand or by machine, either at room temperature or at an elevated temperature. In the third step, shown in FIG. 3C, the drawn distal portion 306 is axially compressed, as shown by arrows 310, to create the convoluted flexible distal portion 312. The axial compression causes the wall of the drawn distal portion 306 to fold into annular convolutions. The wire mandrel 304 maintains the inner lumen 302 in the convoluted flexible distal portion 312 as the drawn distal portion 306 is compressed. If precise control over the external diameter of the convoluted flexible distal portion 312 is desired, a tubular mold (not shown) may be placed over the exterior of the drawn distal portion 306 as it is axially compressed to form the convoluted flexible distal portion 312. The axial compression step may be performed at room temperature or at an elevated temperature. For some polymeric materials, an additional stress relieving or annealing step at an elevated temperature may be required between the drawing step and the axial compression step. FIG. 3D shows an optional fourth step of applying a flexible outer coating 314 to the convoluted flexible distal portion 312. The flexible outer coating 314 may be applied by dissolving a flexible polymer in an appropriate solvent and dipping, spraying or casting one or more layers of the polymer onto the convoluted flexible distal portion 312. Alternatively, the resin and hardener of a flexible thermoset polymer can be mixed and applied to the convoluted flexible distal portion 312 as a liquid by dipping, spraying or casting. The flexible outer coating 314 may also be applied by insert molding a thermoplastic elastomer over the convoluted flexible distal portion 312. The wire mandrel 304 is then withdrawn from the tube 300 and the proximal and distal ends are cut to the desired length to complete the flexible endoscope liner.

Figure 4A:
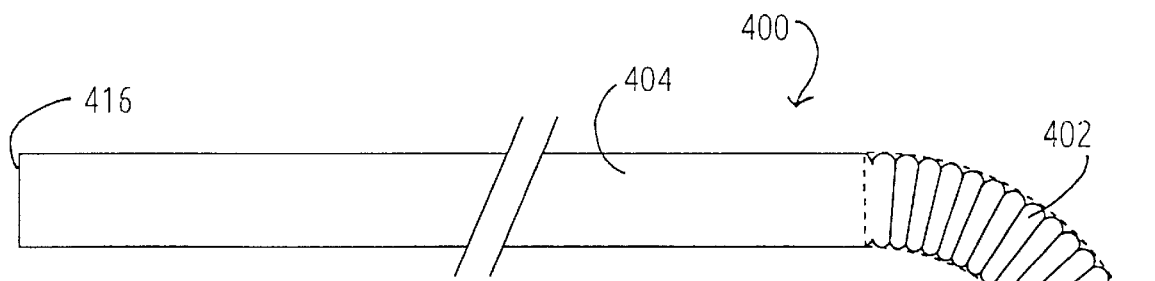
FIG. 4A shows the flexible endoscope liner of FIGS. 1A or 2A bent into a curved configuration as it would be in use.
Figure 4B:
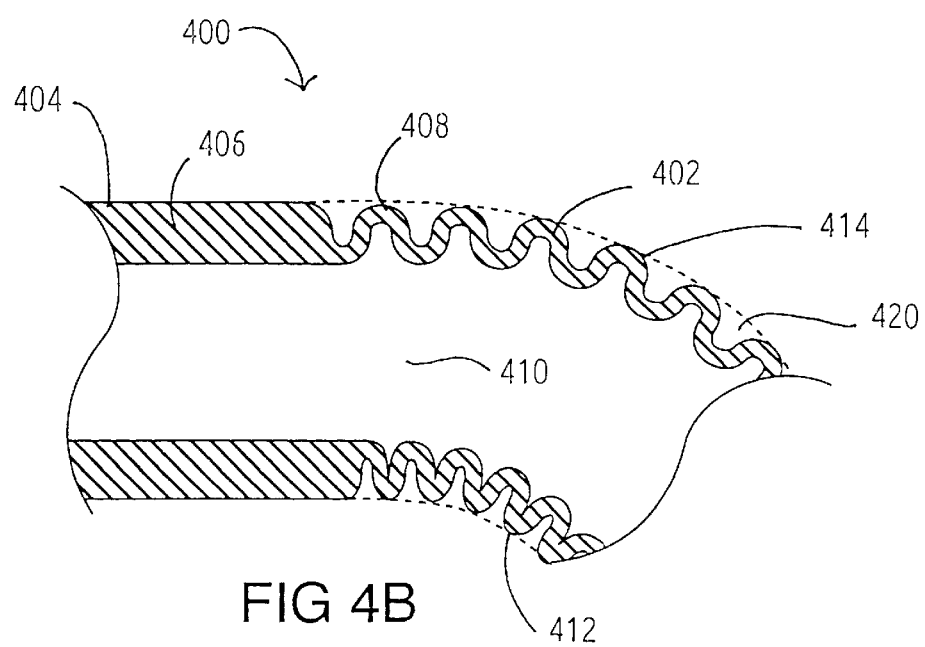
FIG. 4B is a cross section of the flexible distal portion of the flexible endoscope liner of FIG. 4A in the curved configuration.

FIG. 4A shows the flexible endoscope liner 400 of the present invention bent into a curved configuration as it would be in actual clinical use. The flexible endoscope liner 400 shown in FIG. 4A is representative of the flexible endoscope liner in either FIG. 1A (100) or FIG. 2A (200) in use. In use, the flexible endoscope liner 400 is inserted into the working channel of a flexible endoscope (not shown) before the endoscope is inserted into the patient's body through an incision or through a natural body orifice. Once in place, the flexible distal section of the endoscope may be flexed into a curved configuration to view various internal body structures. When the endoscope flexes, the flexible endoscope liner 400 must flex with it. In some applications, the flexible distal section of the endoscope and the flexible endoscope liner 400 may be repeatedly flexed into bends of up to a 180 degrees, with a radius of curvature of 0.5–1.5 inches, as represented in FIG. 4A. FIG. 4B shows a longitudinal cross section of the transition between the relatively inflexible proximal portion 404 and the convoluted flexible distal portion 402 of the flexible endoscope liner 400 of FIG.

4A when it is in the curved configuration. As can be seen in the cross section of FIG. 4B, when the convoluted flexible distal portion 402 of the flexible endoscope liner 400 bends, the convolutions on the inside of the curve 412 compress together and the convolutions on the outside of the curve 414 expand apart. This allows the convoluted flexible distal portion 402 to flex freely with the flexible distal section of the endoscope without kinking or collapsing which would compromise the internal diameter of the inner lumen 410. If the flexible endoscope liner 400 is made with a flexible outer coating 420 over the convoluted flexible distal portion 402, the flexible outer coating 420 (shown in phantom lines) elastically deforms with the convoluted flexible distal portion 402, compressing with the convolutions on the inside of the curve 412 and expanding with the convolutions on the outside of the curve 414.

Figure 5A:
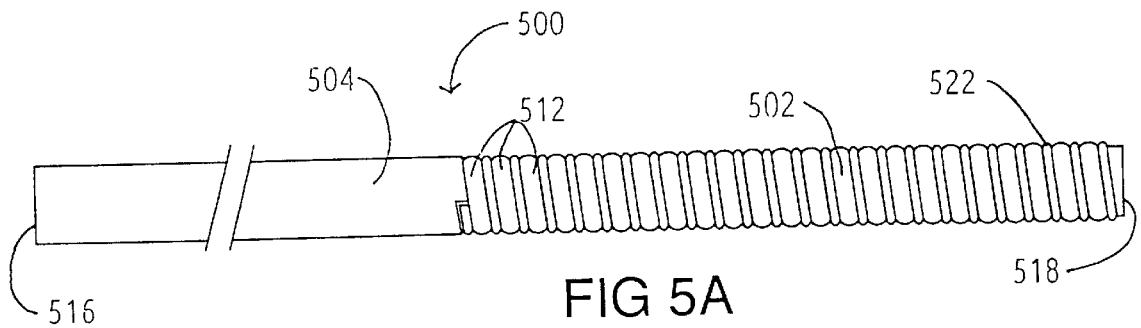
FIG. 5A shows a third embodiment of the flexible endoscope liner with a helically convoluted flexible distal portion having an outer helical reinforcing coil.
Figure 5B:
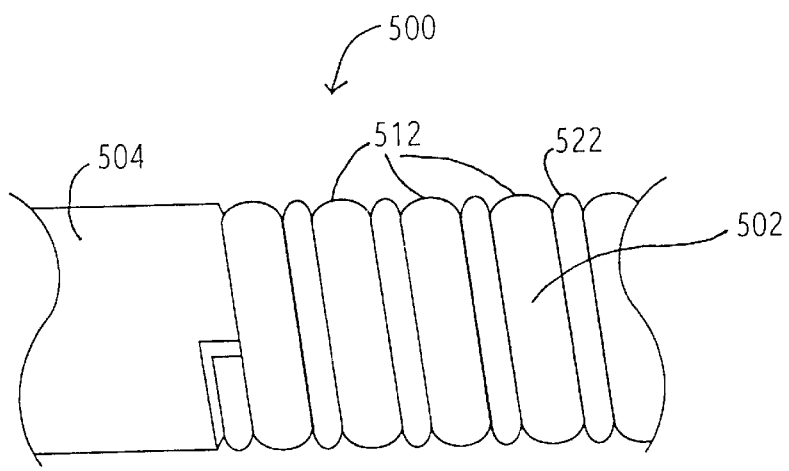
FIG. 5B is an enlarged detail view of the flexible distal portion of the flexible endoscope liner of FIG. 5A.
Figure 5C:
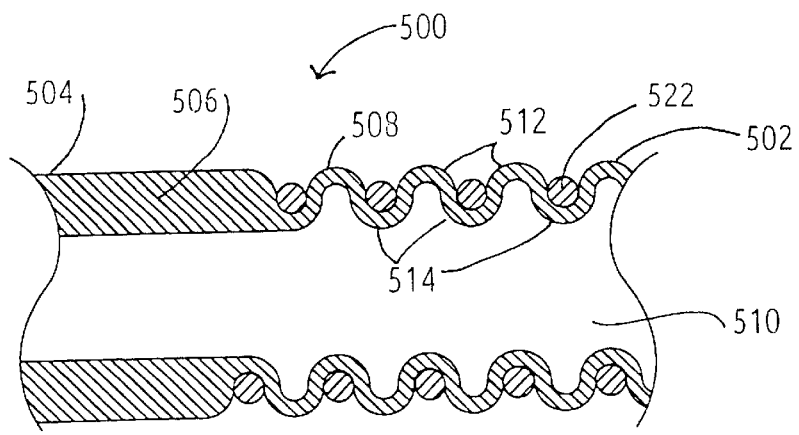
FIG. 5C is a cross section of the flexible distal portion of the flexible endoscope liner of FIG. 5A.

FIG. 5A shows a third embodiment of the flexible endoscope liner 500 with a helically convoluted flexible distal portion 502 having an outer helical reinforcing coil 522. As in the previously described embodiments, the flexible endoscope liner 500 is an elongated tubular member with an inner lumen 510 which extends from the proximal end 516, through a relatively inflexible proximal portion 504 and a flexible distal portion 502, to the distal end 518. FIG. 5B is an enlarged detail view of the flexible endoscope liner 500 of FIG. 5A showing the transition between the relatively inflexible proximal portion 504 and the flexible distal portion 502. FIG. 5C shows a longitudinal cross section of the transition between the relatively inflexible proximal portion 504 and the flexible distal portion 502 of the flexible endoscope liner 500. In contrast to the annular convolutions of the previously described embodiments, the present embodiment has a helically convoluted flexible distal portion 502 which is reinforced with an outer helical reinforcing coil 522. The outer helical reinforcing coil 522 strengthens the thin distal wall 508 and increases the kink resistance of the helically convoluted flexible distal portion 502 without compromising its flexibility.

Preferred materials for the proximal wall 506 and the distal wall 508 of the flexible endoscope liner 500 include fluoropolymers, polyethylenes, polypropylenes, polyolefin copolymers, polyamides, polyamide copolymers, thermoplastic elastomers, polyurethanes, thermoset polymers and composite materials. The outer helical reinforcing coil 522 is preferably made of a resilient, biocompatible, high strength filamentous material, such as metal wire, glass fibers, carbon fibers, high strength polymer fibers or filaments, or a composite material. The cross section of the outer helical reinforcing coil 522 filament may be circular, as shown, rectangular or any other convenient cross section. The filament diameter of the outer helical reinforcing coil 522 is typically from about 0.004 inches to 0.015 inches. The outer diameter of the helical reinforcing coil 522 is typically from about 1.8 mm to 5 mm. In one particularly preferred embodiment, the outer helical reinforcing coil 522 is made of series 300 stainless steel wire (e.g. 302 or 304 stainless steel). The stainless steel wire of the outer helical reinforcing coil 522 is preferably used in a work hardened, unannealed condition (condition B) or slightly stress relieved to a spring temper, because the high strength and excellent resilience of the wire in this condition improves the flexibility characteristics and kink resistance of the helically convoluted flexible distal portion 502. Annealed stainless steel wire or softer alloys are also usable for the outer helical reinforcing coil 522, but it has been found that these softer, more malleable wires do not protect the helically convoluted flexible distal portion 502 as well from kinking or collapse.

Figure 6A:
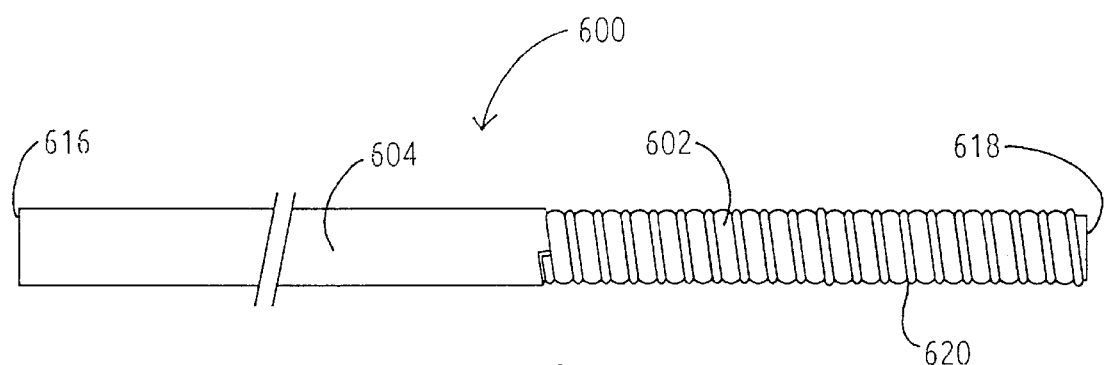
FIG. 6A shows a fourth embodiment of the flexible endoscope liner with a helically convoluted flexible distal portion having a helical reinforcing coil and an outer layer of a flexible polymer.
Figure 6B:
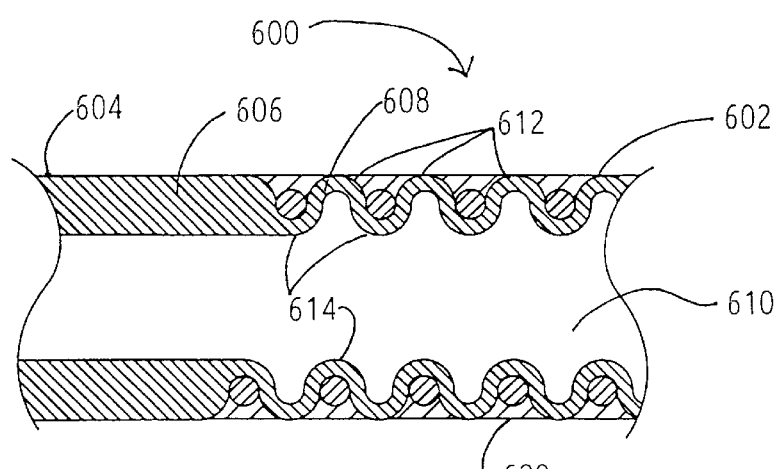
FIG. 6B is a cross section of the flexible distal portion of the flexible endoscope liner of FIG. 6A.

FIG. 6A shows a fourth embodiment of the flexible endoscope liner 600 which is a modification of the flexible endoscope liner 500 shown in FIG. 5A. Similar to the embodiment of FIG. 5A, the flexible endoscope liner 600 is an elongated tubular member with an inner lumen 610 which extends from the proximal end 616, through a relatively inflexible proximal portion 604 and a helically convoluted flexible distal portion 602, to the distal end 618. FIG. 6B is a longitudinal cross section of the flexible endoscope liner 600 showing the transition between the relatively inflexible proximal portion 604 with its relatively thick proximal wall 606 and the helically convoluted flexible distal portion 602 with its thinner distal wall 608 which is reinforced with a outer helical reinforcing coil 622. The helically convoluted flexible distal portion 602 of the flexible endoscope liner 600 has an additional outer layer 620 of a flexible polymer. The flexible outer layer 620 fills in between the peaks of the convolutions 612 and the coils of the outer helical reinforcing coil 622 to create a smooth exterior surface on the helically convoluted flexible distal portion 602. Preferred materials for the flexible outer layer 620 include flexible thermoplastic elastomers, such as ethylene vinyl acetate (EVA), polyamide copolymers (e.g. PEBAX from ELF ATOCHEM) and thermoplastic polyurethanes, and flexible thermoset polymers, such as silicone, latex or thermoset polyurethanes. The hardness of the flexible outer layer 620 material can vary from approximately 50 Shore A durometer to approximately 35 Shore D durometer.

Figure 7A:
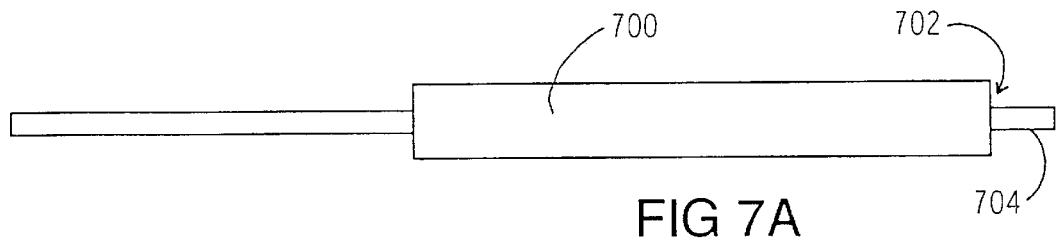
FIGS. 7A, 7B, 7C, 7D and 7E are a series of drawings showing the fabrication steps for the flexible endoscope liners of FIGS. 5A and 6A.
Figure 7B:
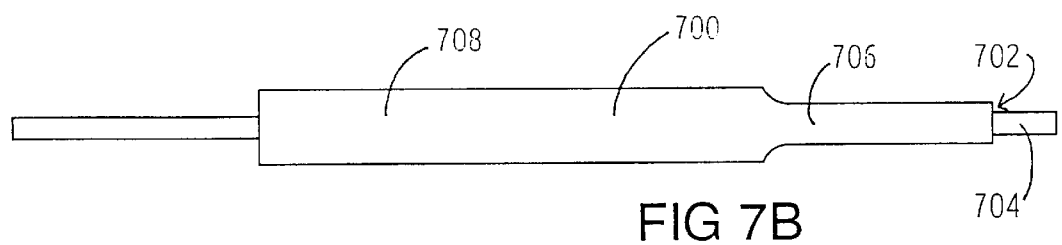
Figure 7C:
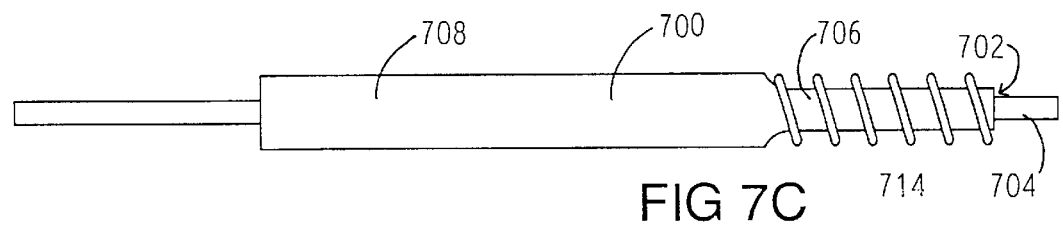
Figure 7D:
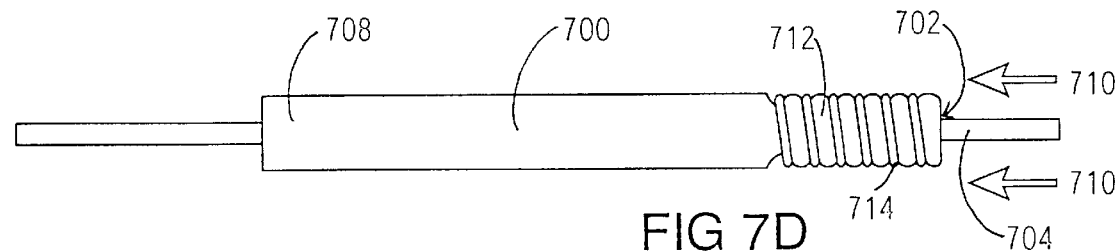
Figure 7E:
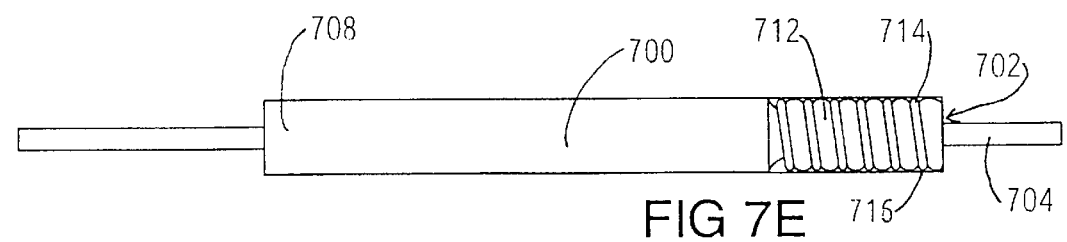

FIGS. 7A, 7B, 7C, 7D and 7E are a series of drawings illustrating one preferred method for fabricating the flexible endoscope liners of FIGS. 5A and 6A. In the first step of the fabrication method shown in FIG. 7A, an extruded polymer tube 700 is cut to an appropriate length and a straightened wire mandrel 704 is inserted into the inner lumen 702 of the tube 700. The wire mandrel 704 is preferably made of stainless steel or another nontoxic, high strength material. The external diameter of the wire mandrel 704 should closely match the internal diameter of the inner lumen 702 with only about 1–3 thousandths of an inch clearance. A nontoxic lubricant or a lubricious coating, such as PTFE, may be used on the wire mandrel 704 to allow easy insertion and removal. In the second step, shown in FIG. 7B, one end of the tube 700 is drawn to reduce its external diameter, thereby creating a drawn distal portion 706 and an undrawn proximal portion 708. The drawing step may be performed by various means appropriate for the material chosen for the extruded polymer tube 700. The drawn distal portion 706 may be created by stretching one end of the extruded polymer tube 700 by hand or by machine, either at room temperature or at an elevated temperature. Alternatively, the drawn distal portion 706 may be created by pulling one end of the extruded polymer tube 700 through a tapered die by hand or by machine, either at room temperature or at an elevated temperature. In the third step, shown in FIG. 7C, a previously made helical reinforcing coil 714 with separated coils is placed over the drawn distal portion 706. In the fourth step, shown in FIG. 7D, the helical reinforcing coil 714 and the drawn distal portion 706 are axially compressed, as shown by arrows 710. The wall of the drawn distal portion 706 folds into a helically convoluted configuration between the coils of the helical reinforcing coil 714 to create the helically convoluted flexible distal portion 712. The wire mandrel 704 maintains the inner lumen 702 in the helically convoluted flexible distal portion 712 as the drawn distal portion 706 is compressed. If precise control over the external diameter of the convoluted flexible distal portion 712 is desired, a tubular mold (not shown) may be placed over the exterior of the drawn distal portion 706 as it is axially compressed to form the helically convoluted flexible distal portion 712. The axial compression step may be performed at room temperature or at an elevated temperature. For some polymeric materials, an additional stress relieving or annealing step at an elevated temperature may be required between the drawing step and the axial compression step. FIG. 7E shows an optional fifth step of applying a flexible outer coating 716 to the convoluted flexible distal portion 712. The flexible outer coating 716 may be applied by dissolving a flexible polymer in an appropriate solvent and dipping, spraying or casting one or more layers of the polymer onto the helically convoluted flexible distal portion 712. Alternatively, the resin and hardener of a flexible thermoset polymer can be mixed and applied to the helically convoluted flexible distal portion 712 as a liquid by dipping, spraying or casting. The flexible outer coating 716 may also be applied by insert molding a thermoplastic elastomer over the helically convoluted flexible distal portion 712. The wire mandrel 704 is then withdrawn from the tube 700 and the proximal and distal ends are cut to the desired length to complete the flexible endoscope liner.

Figure 8A:
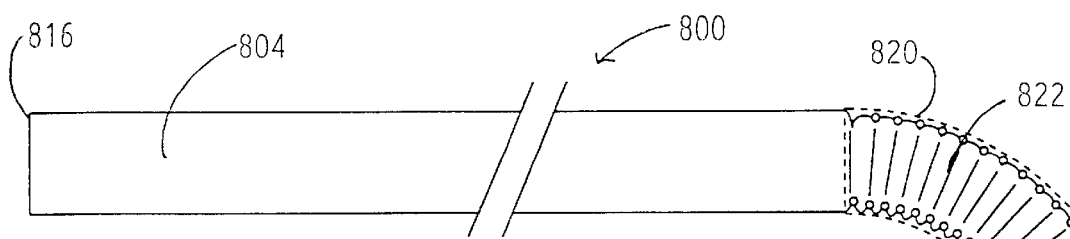
FIG. 8A shows the flexible endoscope liner of FIGS. 5A or 6A bent to a curved configuration as it would be in use.
Figure 8B:
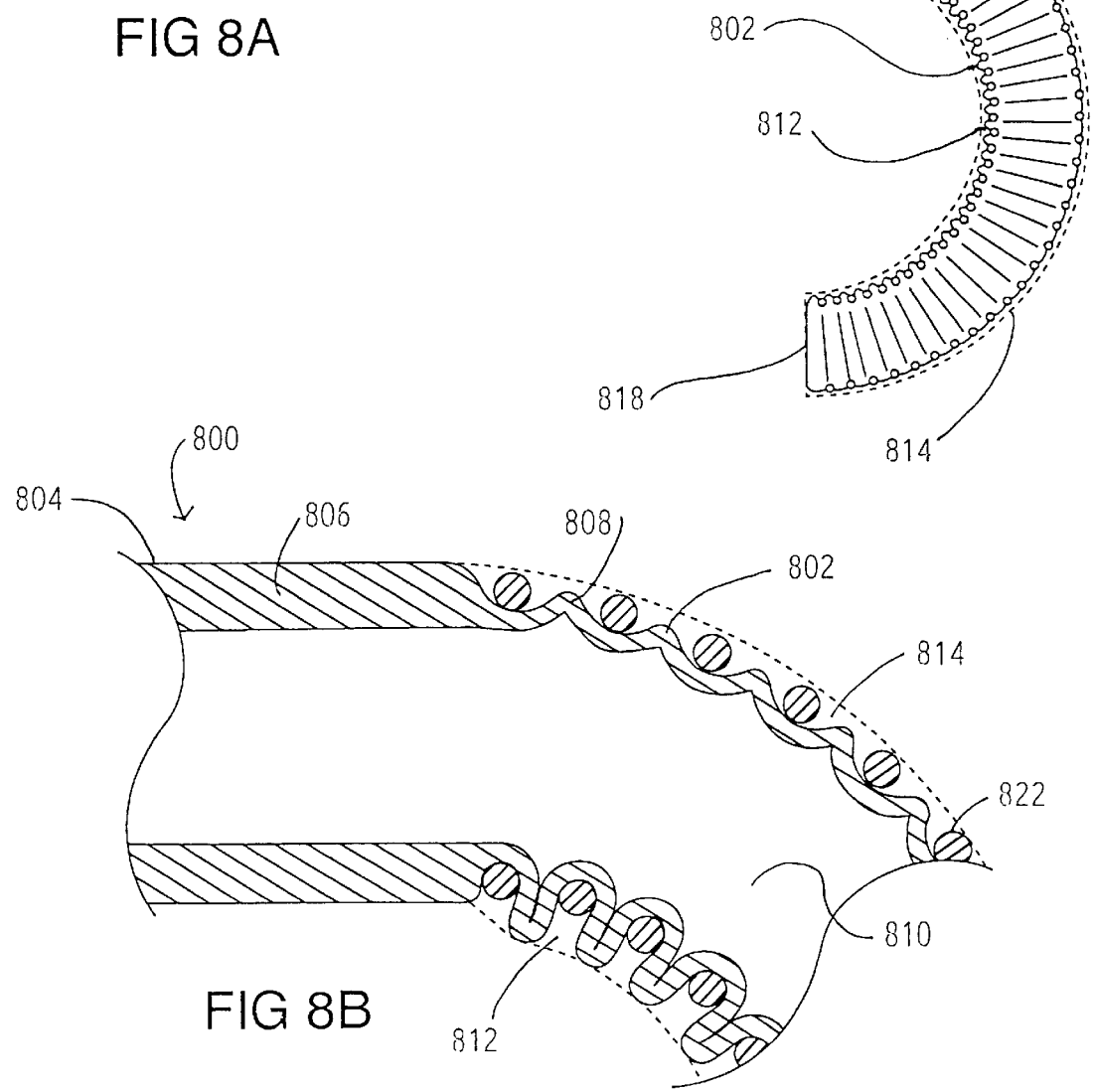
FIG. 8B is a cross section of the flexible distal portion of the flexible endoscope liner of FIG. 8A in the curved configuration.

FIG. 8A shows the flexible endoscope liner 800 of the present invention bent into a curved configuration as it would be in actual clinical use. The flexible endoscope liner 800 shown in FIG. 8A is representative of the flexible endoscope liner in either FIG. 5A (500) or FIG. 6A (600) in use. In use, the flexible endoscope liner 800 is inserted into the working channel of a flexible endoscope (not shown) before the endoscope is inserted into the patient's body through an incision or through a natural body orifice. Once in place, the flexible distal section of the endoscope may be flexed into a curved configuration to view various internal body structures. When the endoscope flexes, the flexible endoscope liner 800 must flex with it. In some applications, the flexible distal section of the endoscope and the flexible endoscope liner 800 may be repeatedly flexed into bends of up to a 180 degrees, with a radius of curvature of 0.5–1.5 inches, as represented in FIG. 8A. FIG. 8B is a longitudinal cross section of the flexible endoscope liner 800 of FIG. 8A in the curved configuration, showing the transition between the relatively inflexible proximal portion 804 and the helically convoluted flexible distal portion 802 reinforced with an outer helical reinforcing coil 822. As can be seen in the cross section of FIG. 8B, when the helically convoluted flexible distal portion 802 of the flexible endoscope liner 800 bends, the convolutions and the reinforcing coils on the inside of the curve 812 compress together and the convolutions and the reinforcing coils on the outside of the curve 814 expand apart. This allows the helically convoluted flexible distal portion 802 to flex freely with the flexible distal section of the endoscope without kinking or collapsing which would compromise the internal diameter of the inner lumen 810. If the flexible endoscope liner 800 is made with a flexible outer coating 820 over the convoluted flexible distal portion 802, the flexible outer coating 820 (shown in phantom lines) elastically deforms with the convoluted flexible distal portion 802, compressing with the convolutions and the reinforcing coils on the inside of the curve 812 and expanding with the convolutions and the reinforcing coils on the outside of the curve 814.

Figure 9A:
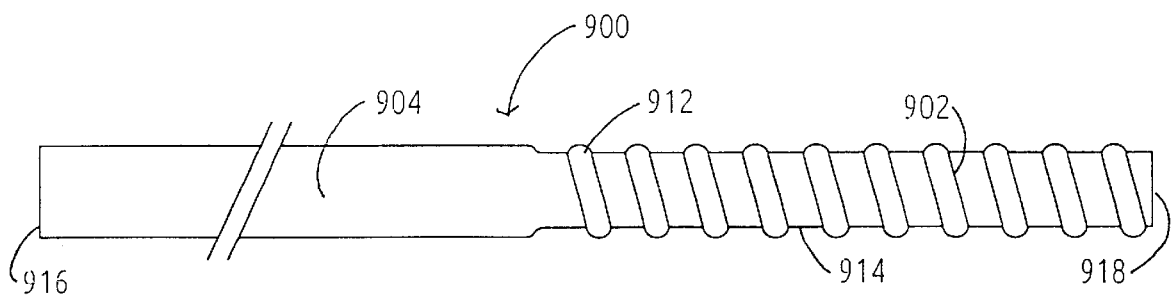
FIG. 9A shows a fifth embodiment of the flexible endoscope liner having a helically threaded flexible distal portion.
Figure 9B:
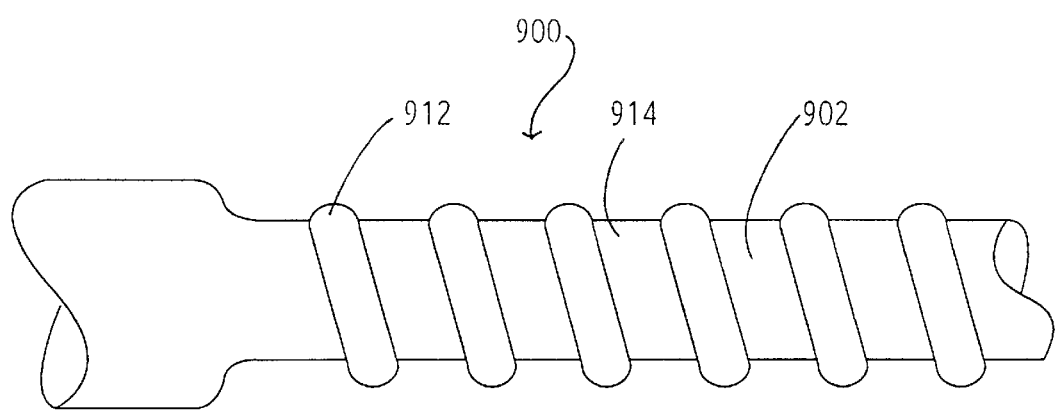
FIG. 9B is an enlarged detail view of the flexible distal portion of the flexible endoscope liner of FIG. 9A.
Figure 9C:
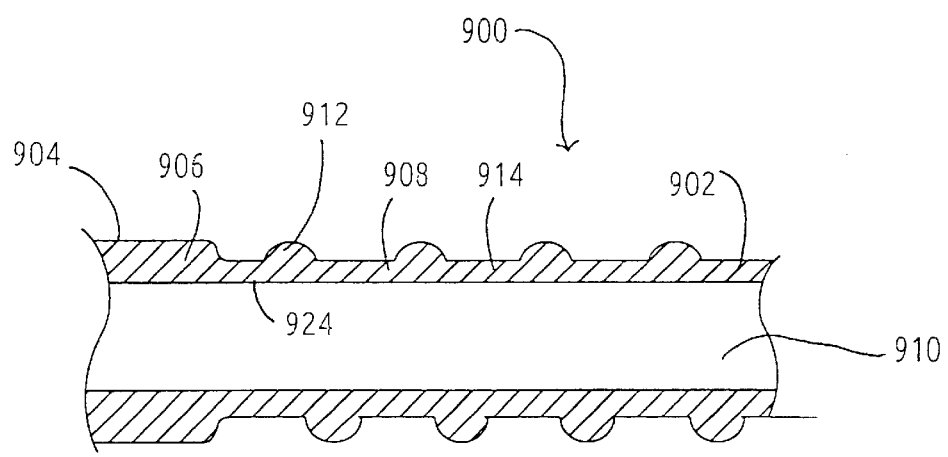
FIG. 9C is a cross section of the helically threaded flexible distal portion of the flexible endoscope liner of FIG. 9A.

FIG. 9A shows a fifth embodiment of the flexible endoscope liner 900 having a helically threaded flexible distal portion 902. As in the previously described embodiments, the flexible endoscope liner 900 is an elongated tubular member with an inner lumen 910 which extends from the proximal end 916, through a relatively inflexible proximal portion 904 and a flexible distal portion 902, to the distal end 918. FIG. 9B is an enlarged detail view of the flexible endoscope liner 900 of FIG. 9A showing the transition between the relatively inflexible proximal portion 904 and the flexible distal portion 902. FIG. 9C shows a longitudinal cross section of the transition between the relatively inflexible proximal portion 904 and the flexible distal portion 902 of the flexible endoscope liner 900. In contrast to the annular or helical convolutions of the previously described embodiments, the present embodiment has a helically threaded flexible distal portion 902. The helically threaded flexible distal portion 902 has an external reinforcing thread 912 that traces a helical path around the distal wall 908 of the flexible endoscope liner 900. A land 914 having a reduced wall thickness traces a helical path around the distal wall 908, separating adjacent turns of the reinforcing thread 912. The width of the lands 914 is typically 100–150 percent of the width of the external reinforcing thread 912. Typically, the thickness of the distal wall 908 at the lands 914 is approximately 60–80 percent of the total wall thickness measured at the peaks of the external reinforcing thread 912. The external reinforcing thread 912 may be made as a single helix, as shown in FIG. 9A, or as a double, triple or multiple helix. The external reinforcing thread 912 may be made with a semicircular profile, as shown in FIG. 9C, or it may be made with a rectangular, triangular, trapezoidal, or semi-elliptical profile or other desired profile. In a particularly preferred embodiment, the proximal wall 906 of the relatively inflexible proximal portion 904 and the distal wall 908 and external reinforcing thread 912 of the helically threaded flexible distal portion 902 are all formed integrally of a single polymeric material. An advantage of this embodiment is that it gives the inner lumen 910 of the flexible endoscope liner 900 a smooth, continuous inner surface 924 for smooth passage of instruments through the working lumen of the endoscope. Suitable materials for this embodiment of the flexible endoscope liner 900 include fluoropolymers, polyethylenes, polypropylenes, polyolefin copolymers, polyamides, polyamide copolymers, thermoplastic elastomers, polyurethanes, thermoset polymers and composite materials.

Typically, the overall length of the flexible endoscope liner 900 is between 30 and 250 cm, and the length of the helically threaded flexible distal portion 102 is between 4 and 25 cm, with the relatively inflexible proximal portion 904 making up the remainder of the length. For some applications, the flexible endoscope liner 900 would be made with the helically threaded flexible distal portion 102 extending the full length of 415 the device. Preferably, the external diameter of the helically threaded flexible distal portion 902, measured at the peaks of the external reinforcing thread 912, is approximately the same as the external diameter of the relatively inflexible proximal portion 904, although, in some applications it may be acceptable to have the external diameter of the helically threaded flexible distal portion 902 larger or smaller than the external diameter of the relatively inflexible proximal portion 904. Typically, the relatively inflexible proximal portion 904 and the helically threaded flexible distal portion 902 have an external diameter of approximately 2.0–4.5 mm and an internal diameter of approximately 1.82–4.0 mm. It should be noted, however, that the length dimensions and the internal and external diameters of the flexible endoscope liner 900 can vary widely depending on the actual design of the endoscope for which it is intended.

Figure 10A:
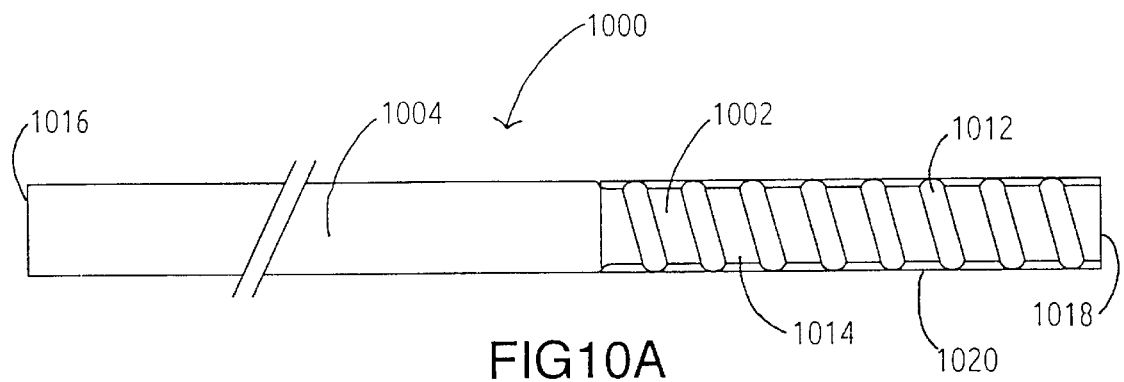
FIG. 10A shows a sixth embodiment of the flexible endoscope liner with a helically threaded flexible distal portion having an outer layer of a flexible polymer.
Figure 10B:
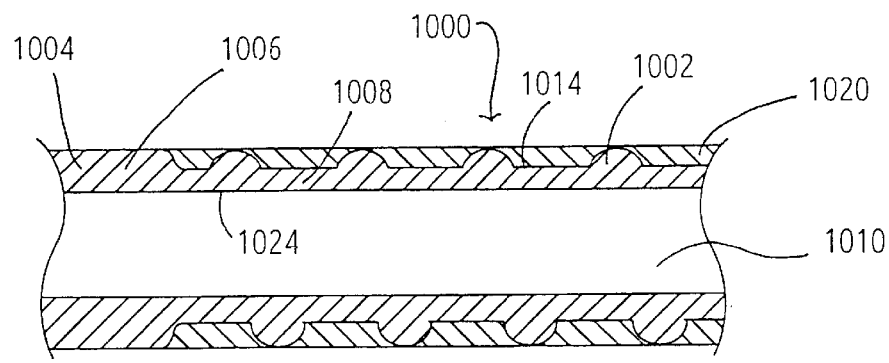
FIG. 10B is a cross section of the flexible distal portion of the flexible endoscope liner of FIG. 10A.

FIG. 10A shows a sixth embodiment of the flexible endoscope liner 1000 which is a modification of the flexible endoscope liner 900 shown in FIG. 9A. Similar to the embodiment of FIG. 9A, the flexible endoscope liner 1000 is an elongated tubular member with an inner lumen 1010 which extends from the proximal end 1016, through a relatively inflexible proximal portion 1004 and a helically threaded flexible distal portion 1002, to the distal end 1018. FIG. 10B is a longitudinal cross section of the flexible endoscope liner 1000 showing the transition between the relatively inflexible proximal portion 1004 and the helically threaded flexible distal portion 1102. The relatively inflexible proximal portion 1004 has a relatively thick proximal wall 1006 and the helically threaded flexible distal portion 1102 has a thinner distal wall 1008 reinforced by an external reinforcing thread 1012. The helically threaded flexible distal portion 1002 of the flexible endoscope liner 1000 has an additional outer layer 1020 of a flexible polymer. The flexible outer layer 1020 fills in the lands 1014 between the peaks of the external reinforcing thread 1012 to create a smooth exterior surface on the helically threaded flexible distal portion 1002. Preferred materials for the flexible outer layer 1020 include flexible thermoplastic elastomers, such as ethylene vinyl acetate (EVA), polyamide copolymers (e.g. PEBAX from ELF ATOCHEM) and thermoplastic polyurethanes, and flexible thermoset polymers, such as silicone, latex or thermoset polyurethanes. The hardness of the flexible outer layer 1020 material can vary from approximately 50 Shore A durometer to approximately 35 Shore D durometer.

Figure 11A:
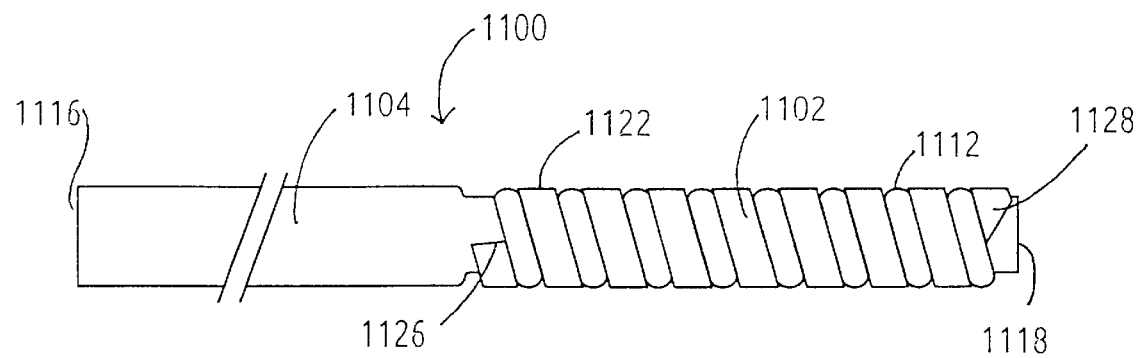
FIG. 11A shows a seventh embodiment of the flexible endoscope liner with a helically threaded flexible distal portion having an outer helical reinforcing coil.
Figure 11B:
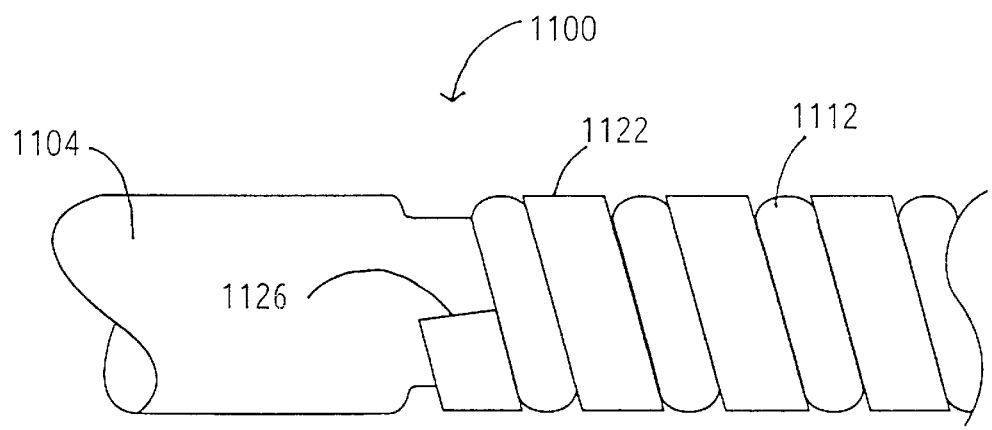
FIG. 11B is an enlarged detail view of the flexible distal portion of the flexible endoscope liner of FIG. 11A.
Figure 11C:
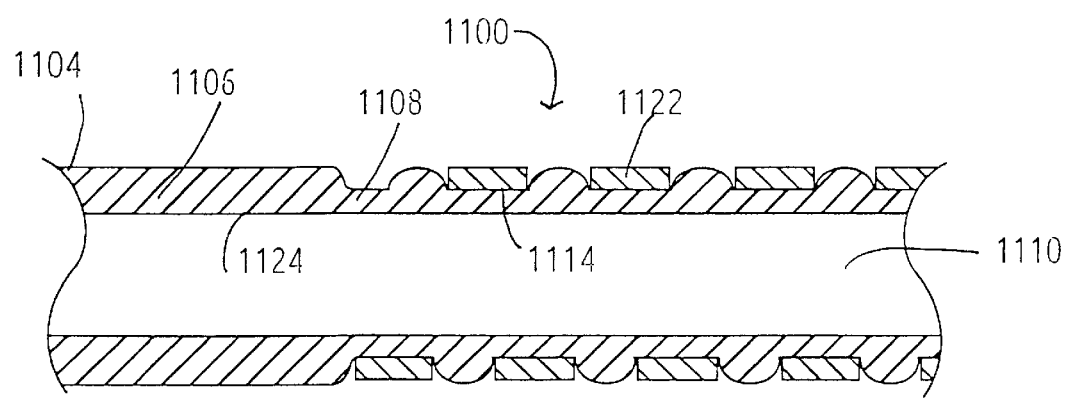
FIG. 11C is a cross section of the flexible distal portion of the flexible endoscope liner of FIG. 11A.

FIG. 11A shows a seventh embodiment of the flexible endoscope liner 1100 which is another modification of the flexible endoscope liner 900 shown in FIG. 9A. Similar to the embodiment of FIG. 9A, the flexible endoscope liner 1100 is an elongated tubular member with an inner lumen 1110 which extends from the proximal end 1116, through a relatively inflexible proximal portion 1104 and a helically threaded flexible distal portion 1102, to the distal end 1118. FIG. 11B is a longitudinal cross section of the flexible endoscope liner 1100 showing the transition between the relatively inflexible proximal portion 1104 and the helically threaded flexible distal portion 1102. The relatively inflexible proximal portion 1104 has a relatively thick proximal wall 1106 and the helically threaded flexible distal portion 1102 has a thinner distal wall 1108 reinforced by an external reinforcing thread 1112. The helically threaded flexible distal portion 1102 of the flexible endoscope liner 1100 has an additional outer helical reinforcing coil 1122 which occupies the lands 1114 between the peaks of the external reinforcing thread 1112. The outer helical reinforcing coil 1122 strengthens the thin distal wall 1108 and increases the kink resistance of the helically threaded flexible distal portion 1102 without compromising its flexibility.

The outer helical reinforcing coil 1122 is preferably made of a resilient, biocompatible, high strength filamentous material, such as metal wire, glass fibers, carbon fibers, high strength polymer fibers or filaments, or a composite material. The cross section of the outer helical reinforcing coil 1122 may be rectangular, as shown, circular or any other convenient cross section. In a rectangular configuration, the filament width of the outer helical reinforcing coil 1122 is typically 0.008–0.020 inches and the thickness is typically 0.003–0.015 inches. In one particularly preferred embodiment, the outer helical reinforcing coil 1122 is made of rectangular cross section series 300 stainless steel wire (e.g. 302 or 304 stainless steel) with dimensions of approximately 0.015 by 0.004 inches. Preferably, the outer helical reinforcing coil 1122 is trimmed to length with a square cut proximal end 1126 and an angle cut distal end 1128. The stainless steel wire of the outer helical reinforcing coil 1122 is preferably used in a work hardened, unannealed condition (condition B) or slightly stress relieved to a spring temper, because the high strength and excellent resilience of the wire in this condition improves the flexibility characteristics and kink resistance of the helically convoluted flexible distal portion 1102. Annealed stainless steel wire or softer alloys are also usable for the outer helical reinforcing coil 1122, but it has been found that these softer, more malleable wires do not protect the helically convoluted flexible distal portion 1102 as well from kinking or collapse.

Figure 12A:
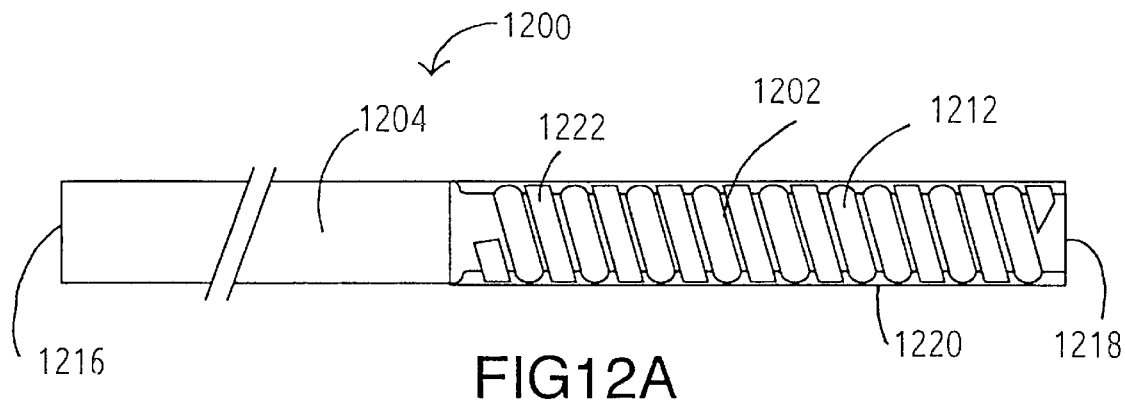
FIG. 12A shows an eighth embodiment of the flexible endoscope liner with a helically threaded flexible distal portion having a helical reinforcing coil and an outer layer of a flexible polymer.
Figure 12B:
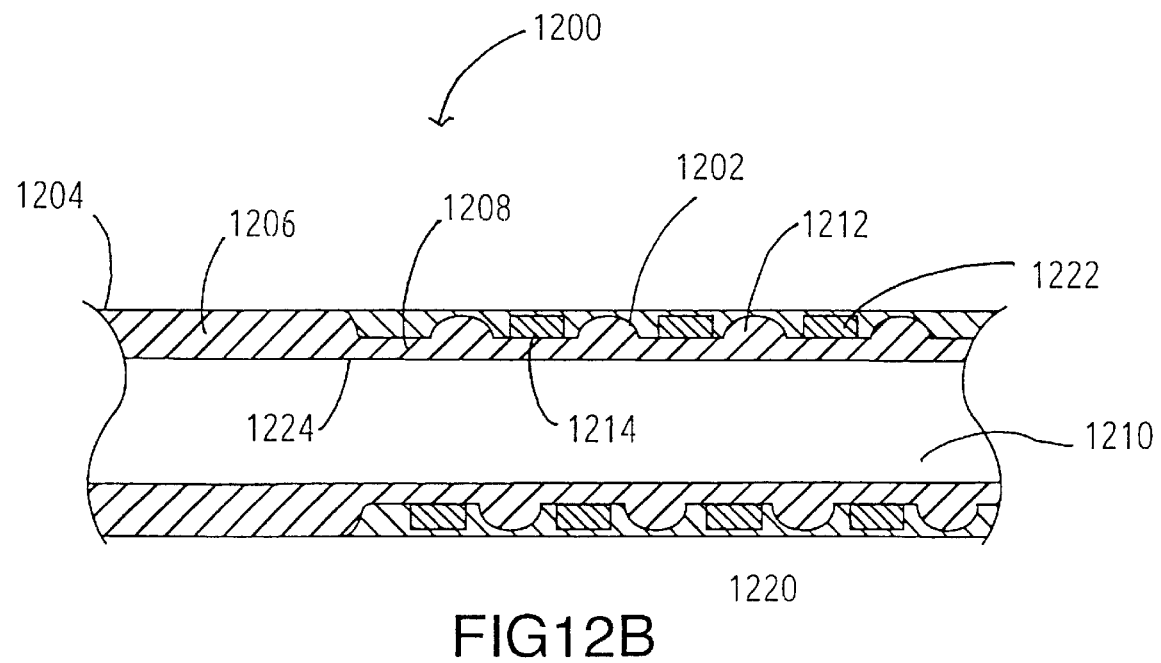
FIG. 12B is a cross section of the flexible distal portion of the flexible endoscope liner of FIG. 12A.

FIG. 12A shows an eighth embodiment of the flexible endoscope liner 1200 that combines the features of the flexible endoscope liners shown in FIG. 10A (1000) and FIG. 11A (1100). The flexible endoscope liner 1200 is an elongated tubular member with an inner lumen 1220 which extends from the proximal end 1226, through a relatively inflexible proximal portion 1204 and a helically threaded flexible distal portion 1202, to the distal end 1228. FIG. 12B is a longitudinal cross section of the flexible endoscope liner 1200 showing the transition between the relatively inflexible proximal portion 1204 and the helically threaded flexible distal portion 1202. The relatively inflexible proximal portion 1204 has a relatively thick proximal wall 1206 and the helically threaded flexible distal portion 1202 has a thinner distal wall 1208 reinforced by an external reinforcing thread 1222. The helically threaded flexible distal portion 1202 of the flexible endoscope liner 1200 has an outer helical reinforcing coil 1222 which occupies the lands 1224 between the peaks of the external reinforcing thread 1222. The outer helical reinforcing coil 1222 strengthens the thin distal wall 1208 and increases the kink resistance of the helically threaded flexible distal portion 1202 without compromising its flexibility. The helically threaded flexible distal portion 1202 of the flexible endoscope liner 1200 also has an additional outer layer 1220 of a flexible polymer. The flexible outer layer 1220 fills in the lands 1214 between the peaks of the external reinforcing thread 1212 and the coils of the outer helical reinforcing coil 1222 to create a smooth exterior surface on the helically threaded flexible distal portion 1202. Preferred materials for the flexible outer layer 1220 include flexible thermoplastic elastomers, such as ethylene vinyl acetate (EVA), polyamide copolymers (e.g. PEBAX from ELF ATOCHEM) and thermoplastic polyurethanes, and flexible thermoset polymers, such as silicone, latex or thermoset polyurethanes. The hardness of the flexible outer layer 1220 material can vary from approximately 50 Shore A durometer to approximately 35 Shore D durometer.

FIGS. 13A, 13B, 13C, 13D and 13E are a series of drawings illustrating one preferred method for fabricating the flexible endoscope liners of FIGS. 9A, 10A, 11A and 12A. In the first step of the fabrication method shown in FIG. 13A, an extruded polymer tube 1300 is cut to an appropriate length and a straightened wire mandrel 1304 is inserted into the inner lumen 1302 of the tube 1300. The wire mandrel 1304 is preferably made of stainless steel or another nontoxic, high strength material. The external diameter of the wire mandrel 1304 should closely match the internal diameter of the inner lumen 1302 with only about 1–3 thousandths of an inch clearance. A nontoxic lubricant or a lubricious coating, such as PTFE, may be used on the wire mandrel 1304 to allow easy insertion and removal. In the second step, shown in FIG. 13B, an external helical thread is formed on one end of the tube 1300, to create a threaded distal portion 1306 and an unthreaded proximal portion 1308. The threading step may be performed by hand or by machine using various means appropriate for the material chosen for the extruded polymer tube 1300. One method for forming the threaded distal portion 1306 on the end of the tube 1300, involves placing the tube 1300 over a wire mandrel and rotating the tube 1300 in contact with a cutting tool which advances along the length of the tube 1300 to cut a helical thread into the wall of the tube 1300. Alternatively, a deforming tool can be used in place of the cutting tool to form a helical thread in the wall of the tube 1300 by deforming the material without cutting. Depending on the characteristics of the material of the polymer tube 1300, the thread forming step can be performed at room temperature or at an elevated temperature by heating either the thread forming tool or the polymer of the tube 1300. The threaded distal portion 1306 may also be created by drawing one end of the extruded polymer tube 1300 through a threading die, while rotating either the tube 1300 or the threading die, to cut a helical thread into the wall of the tube 1300. Alternatively, the threaded distal portion 1306 may be made by drawing one end of the extruded polymer tube 1300 through a threading die which deforms the walls of the tube 1300 into a helically threaded configuration without cutting. Once again, depending on the characteristics of the material chosen for the polymer tube 1300, the thread forming step can be performed at room temperature or at an elevated temperature by heating either the threading die or the polymer of the tube 1300. At this point, the flexible endoscope liner is in the form of the flexible endoscope liner 900 of FIG. 9A. Alternatively to steps one and two, the entire flexible endoscope liner, including the threaded distal portion 1306 and an unthreaded proximal portion 1308, can be injection molded in one step.

Figure 13A:
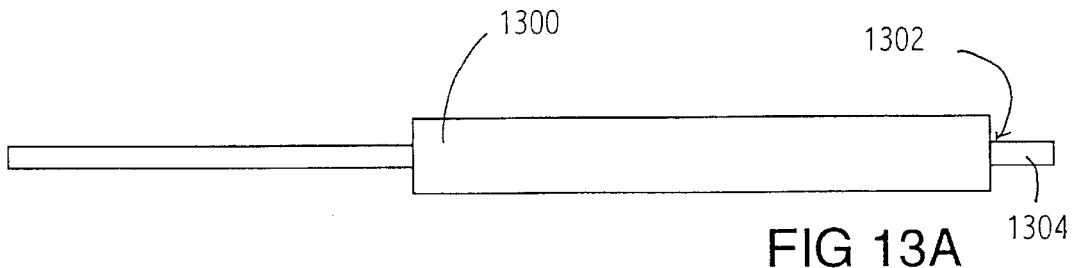
FIGS. 13A, 13B, 13C, 13D and 13E are a series of drawings showing the fabrication steps for the flexible endoscope liners of FIGS. 9A, 10A, 11A and 12A.
Figure 13B:
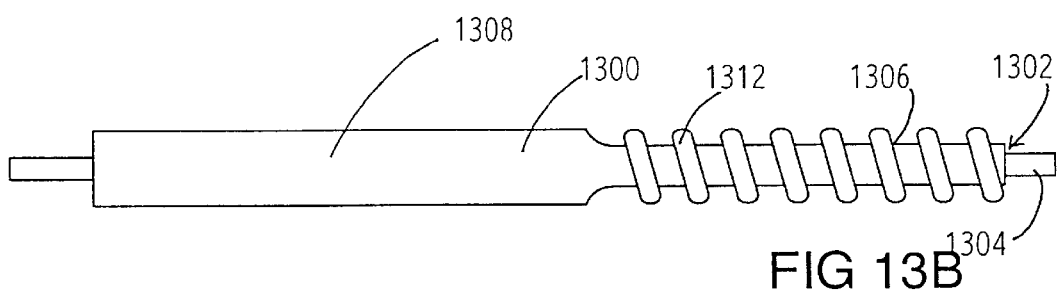
Figure 13C:
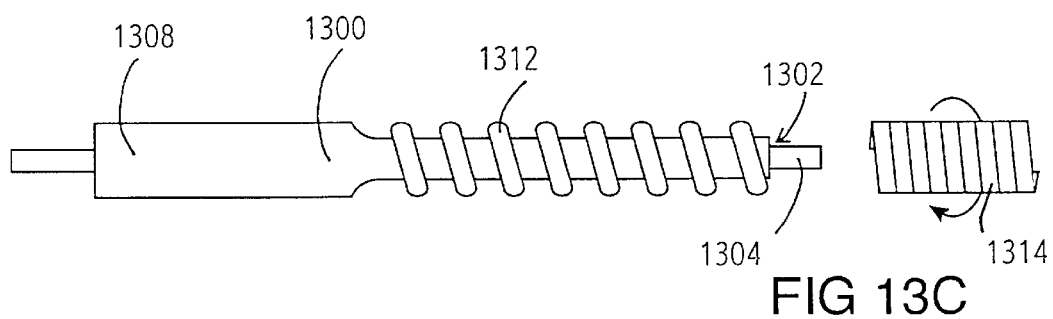
Figure 13D:
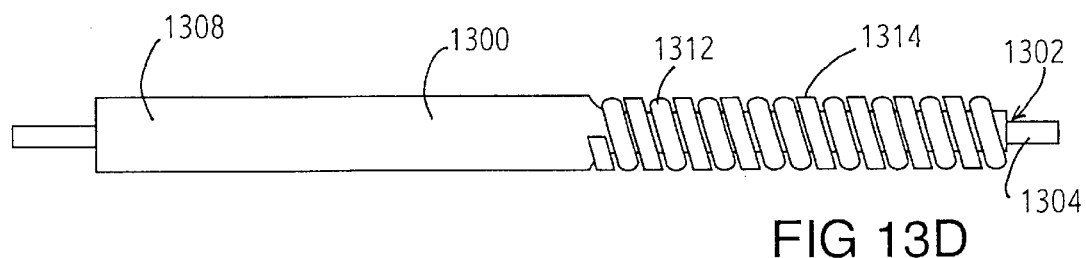

In an optional third step, shown in FIGS. 13C and 13D, a previously made helical reinforcing coil 1314 is threaded onto the threaded distal portion 1306. After the helical reinforcing coil 1314 is assembled onto the threaded distal portion 1306, the flexible endoscope liner in FIG. 13D is in the form of the flexible endoscope liner 1100 of FIG. 11A.

Figure 13E:
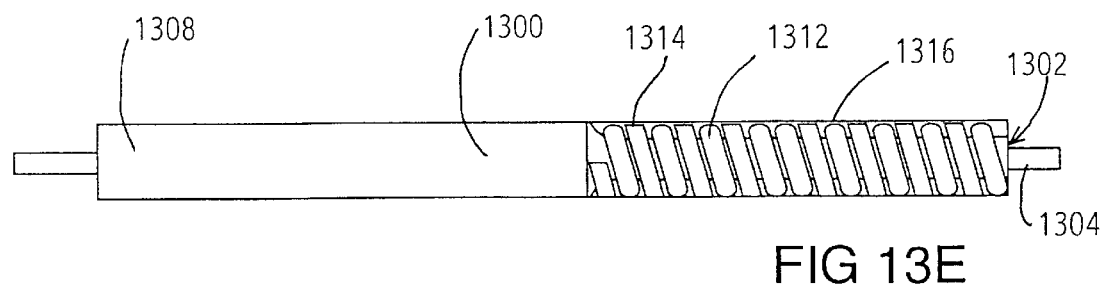

FIG. 13E shows an optional fourth step of applying a flexible outer coating 1316 to the threaded flexible distal portion 1312 and the helical reinforcing coil 1314. The flexible outer coating 1316 may be applied by dissolving a flexible polymer in an appropriate solvent and dipping, spraying or casting one or more layers of the polymer onto the helically convoluted flexible distal portion 1312. Alternatively, the resin and hardener of a flexible thermoset polymer can be mixed and applied to the helically convoluted flexible distal portion 1312 as a liquid by dipping, spraying or casting. The flexible outer coating 1316 may also be applied by insert molding a thermoplastic elastomer over the helically convoluted flexible distal portion 1312. The wire mandrel 1304 is then withdrawn from the tube 1300 and the proximal and distal ends are cut to the desired length to complete the flexible endoscope liner. After the flexible outer coating 1316 is applied, the flexible endoscope liner in FIG. 13E in is the form of the flexible endoscope liner 1200 of FIG. 12A.

Alternatively, the second step of FIGS. 13C and 13D may be bypassed, and the flexible outer coating 1316 applied directly to the threaded flexible distal portion 1312 in FIG. 13B to create a flexible endoscope liner in the form of the flexible endoscope liner 1000 of FIG. 10A.

Figure 14A:
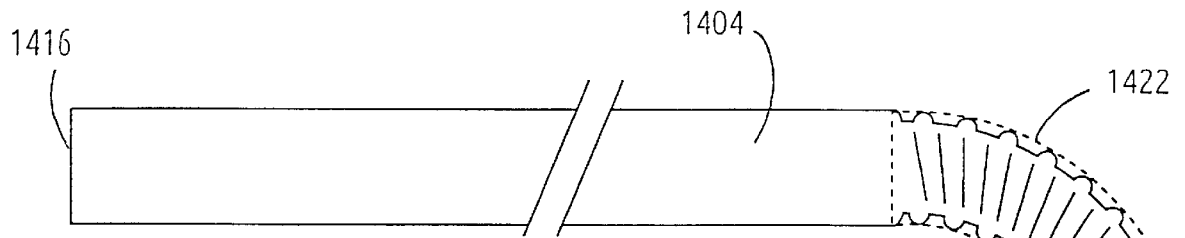
FIG. 14A shows the flexible endoscope liner of FIGS. 9A, 10A, 11A or 12A bent to a curved configuration as it would be in use.
Figure 14B:
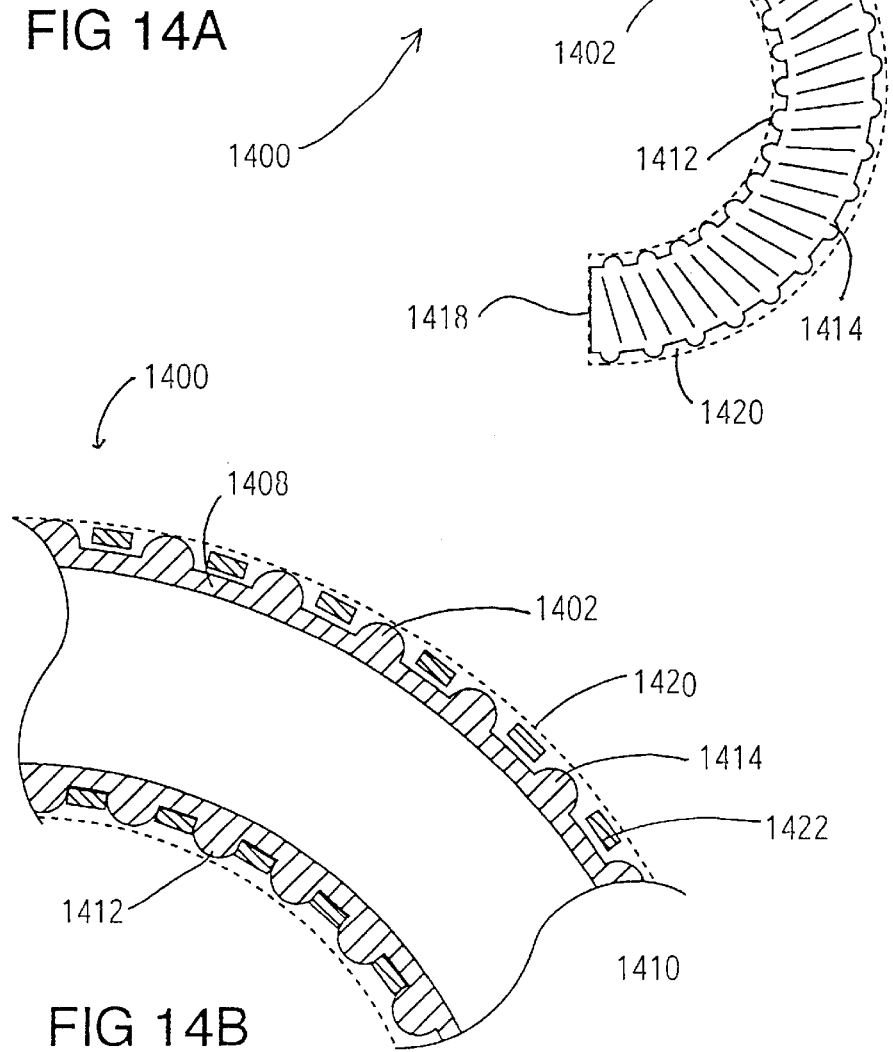
FIG. 14B is a cross section of the flexible distal portion of the flexible endoscope liner of FIG. 14A in the curved configuration.

FIG. 14A shows the flexible endoscope liner 1400 of the present invention bent into a curved configuration as it would be in actual clinical use. The flexible endoscope liner 1400 shown in FIG. 14A is representative of the flexible endoscope liner in either FIG. 9A (900), FIG. 10A (1000), FIG. 11A (1100) or FIG. 12A (1200) in use. In use, the flexible endoscope liner 1400 is inserted into the working channel of a flexible endoscope (not shown) before the endoscope is inserted into the patient's body through an incision or through a natural body orifice. Once in place, the flexible distal section of the endoscope may be flexed into a curved configuration to view various internal body structures. When the endoscope flexes, the flexible endoscope liner 1400 must flex with it. In some applications, the flexible distal section of the endoscope and the flexible endoscope liner 1400 may be repeatedly flexed into bends of up to a 180 degrees, with a radius of curvature of 0.5–8.0 inches, as represented in FIG. 14A. FIG. 14B is a longitudinal cross section of the flexible endoscope liner 1400 of FIG. 14A in the curved configuration, showing the transition between the relatively inflexible proximal portion 1404 and the helically threaded flexible distal portion 1402, optionally reinforced with an outer helical reinforcing coil 1422. As can be seen in the cross section of FIG. 14B, when the helically threaded flexible distal portion 1402 of the flexible endoscope liner 1400 bends, the threads and the reinforcing coils on the inside of the curve 1412 compress together slightly and the threads and the reinforcing coils on the outside of the curve 1414 expand apart slightly. This allows the helically threaded flexible distal portion 1402 to flex freely with the flexible distal section of the endoscope without kinking or collapsing which would compromise the internal diameter of the inner lumen 1410. If the flexible endoscope liner 1400 is made with a flexible outer coating 1420 over the threaded flexible distal portion 1402, the flexible outer coating 1420 (shown in phantom lines) elastically deforms with the threaded flexible distal portion 1402, compressing with the threads and the reinforcing coils on the inside of the curve 1412 and expanding with the threads and the reinforcing coils on the outside of the curve 1414.

All of the various constructions and manufacturing methods for the disposable flexible inner liner of the present invention described above will also be advantageous for constructing a flexible tubular member for use in a variety of catheters for diagnostic or therapeutic purposes. The flexible tubular member may be used alone as a diagnostic or therapeutic catheter, a guiding catheter or a catheter introducer, with only minor modifications, such as adding a Luer lock hub or other catheter fitting to the proximal end of the device. Alternatively, the flexible tubular member may also be used as one component of a more complex catheter device or a catheter system. The benefits of the disposable flexible inner liner construction as a flexible tubular member can be used to add the properties of flexibility, kink resistance and an uncompromised inner lumen to the performance of any catheter. The flexible tubular member construction may find its way into the construction of cardiovascular catheters, urology catheters, visceral catheters catheter introducers and a wide variety of other catheters, as well as minimally invasive surgical devices. For catheter applications such as these, the outer diameter of the flexible tubular member would typically be from 1 mm to 3 mm, but could range from 0.5 mm to 10 mm for some applications. The length of the flexible tubular member for use in catheter applications would typically range from 10 cm to 300 cm. Catheters and surgical devices made using a flexible tubular member built according to the disposable flexible inner liner construction of the present invention can be introduced into the body through the working channel of an endoscope or they can be introduced independently under endoscopic, fluoroscopic or ultrasonic guidance.

What is claimed is:

1. A collapse-resistant and kink-resistant, flexible tubing construction comprising:
   a tubular member having a proximal end and a distal end and at least one lumen extending therebetween, said tubular member having a tubular wall surrounding said at least one lumen,
   at least a first portion of said tubular member having a multiplicity of external ridge means for allowing said first portion of said tubular member to flex without kinking or buckling of said tubular wall and without collapsing said at least one lumen, wherein said multiplicity of external ridge means are formed by sequential turns of at least one helical external ridge on said tubular wall within said first portion,
   and a helical reinforcing member positioned within an external trough between subsequent turns of said at least one helical external ridge on said tubular wall,
   wherein said external trough between subsequent turns of said at least one helical external ridge is filled with a soft, flexible material covering said helical reinforcing member.

2. The tubing construction of claim 1 wherein said multiplicity of external ridge means are formed by convolutions of said tubular wall within said first portion of said tubular member.

3. The tubing construction of claim 1 wherein said at least one helical external ridge on said tubular wall is formed by at least one external helical thread appended to said tubular wall.

4. The tubing construction of claim 3 wherein said external helical thread has a semicircular profile.

5. The tubing construction of claim 1 wherein said tubular member further comprises a relatively inflexible second portion.

6. The tubing construction of claim 5 wherein said first portion of said tubular member has a first internal diameter and said second portion of said tubular member has a second internal diameter, said first internal diameter being approximately equal to said second internal diameter.

7. The tubing construction of claim 6 wherein said first portion of said tubular member has a first external diameter and said second portion of said tubular member has a second external diameter, said first external diameter being approximately equal to said second external diameter.

8. A collapse-resistant and kink-resistant, flexible tubing construction comprising:
   a tubular member having a proximal end and a distal end and at least one lumen extending therebetween, said tubular member having a tubular wall surrounding said at least one lumen,
   at least a first portion of said tubular member having a multiplicity of external ridge means for allowing, said first portion of said tubular member to flex without kinking or buckling, of said tubular wall and without collapsing said at least one lumen, wherein said multiplicity of external ridge means are formed by sequential turns of at least one helical external ridge on said tubular wall within said first portion,
   and a helical reinforcing member positioned within an external trough between subsequent turns of said at least one helical external ridge on said tubular wall, said helical reinforcing member having an approximately rectangular cross section.

9. The tubing construction of claim 8 wherein said at least one helical external ridge on said tubular wall is formed by a helical convolution of said tubular wall within said first portion.

10. The tubing construction of claim 8 wherein said external trough between subsequent turns of said at least one helical external ridge is filled with a soft, flexible material covering said helical reinforcing member.

11. The tubing construction of claim 8 wherein said at least one helical external ridge on said tubular wall is formed by at least one external helical thread appended to said tubular wall.

12. The tubing construction of claim 11 wherein said external helical thread has a semicircular profile.

13. The tubing construction of claim 8 wherein said tubular member further comprises a relatively inflexible second portion.

14. The tubing construction of claim 13 wherein said first portion of said tubular member has a first internal diameter and said second portion of said tubular member has a second internal diameter, said first internal diameter being approximately equal to said second internal diameter.

15. The tubing construction of claim 14 wherein said first portion of said tubular member has a first external diameter and said second portion of said tubular member has a second external diameter, said first external diameter being approximately equal to said second external diameter.

16. In combination:
   an endoscope or borescope having at least one scope lumen extending therethrough; and
   a tubular member positioned within said scope lumen, said tubular member having a proximal end and a distal end and at least one internal lumen extending therebetween, said tubular member having a tubular wall surrounding said at least one internal lumen, at least a first portion of said tubular member having a multiplicity of external ridge means for allowing said first portion of said tubular member to flex without kinking or buckling of said tubular wall and without collapsing said at least one internal lumen, said multiplicity of external ridge means being formed by convolutions of said tubular wall within said first portion of said tubular member, said first portion of said tubular member having external troughs and wherein said external troughs are filled with a soft, flexible material.

17. The combination of claim 16 wherein said multiplicity of external ridge means are formed by sequential turns of at least one helical external ridge on said tubular wall within said first portion.

18. The combination of claim 17 further comprising a helical reinforcing member positioned within an external trough between subsequent turns of said at least one helical external ridge on said tubular wall.

19. The combination of claim 16 wherein said tubular member further comprises a relatively inflexible second portion.

20. In combination:
   an endoscope or borescope having at least one scope lumen extending therethrough; and
   a tubular member positioned within said scope lumen, said tubular member having a proximal end and a distal end and at least one internal lumen extending therebetween, said tubular member having a tubular wall surrounding said at least one internal lumen, at least a first portion of said tubular member having a multiplicity of external ridge means for allowing said first portion of said tubular member to flex without kinking or buckling of said tubular wall and without collapsing said at least one internal lumen, wherein said multiplicity of external ridge means are formed by sequential turns of at least one helical external ridge on said tubular wall within said first portion, and a helical reinforcing member positioned within an external trough between subsequent turns of said at least one helical external ridge on said tubular wall, wherein said external trough between subsequent turns of said at least one helical external ridge is filled with a soft, flexible material covering said helical reinforcing member.

21. The combination of claim 20 wherein said multiplicity of external ridge means are formed by convolutions of said tubular wall within said first portion of said tubular member.

22. The combination of claim 20 wherein said tubular member further comprises a relatively inflexible second portion.

\* \* \* \* \*